(12) United States Patent
Nakamura et al.

(10) Patent No.: US 10,519,103 B2
(45) Date of Patent: Dec. 31, 2019

(54) UREA PRODUCTION METHOD

(71) Applicant: TOYO ENGINEERING CORPORATION, Chiyoda-ku, Tokyo (JP)

(72) Inventors: Shuhei Nakamura, Narashino (JP); Keigo Sasaki, Narashino (JP)

(73) Assignee: TOYO ENGINEERING CORPORATION, Tokyo (JP)

( * ) Notice: Subject to any disclaimer, the term of this patent is extended or adjusted under 35 U.S.C. 154(b) by 0 days.

(21) Appl. No.: 15/553,527

(22) PCT Filed: Apr. 1, 2016

(86) PCT No.: PCT/JP2016/060884
§ 371 (c)(1),
(2) Date: Aug. 24, 2017

(87) PCT Pub. No.: WO2016/159336
PCT Pub. Date: Oct. 6, 2016

(65) Prior Publication Data
US 2018/0037542 A1    Feb. 8, 2018

(30) Foreign Application Priority Data

Apr. 1, 2015    (JP) .................................. 2015-075025

(51) Int. Cl.
*C07C 273/16*    (2006.01)
*C07C 273/14*    (2006.01)
(Continued)

(52) U.S. Cl.
CPC ............... *C07C 273/16* (2013.01); *B01J 2/00* (2013.01); *B01J 2/16* (2013.01); *B01J 2/30* (2013.01); *C07C 273/14* (2013.01)

(58) Field of Classification Search
None
See application file for complete search history.

(56) References Cited

U.S. PATENT DOCUMENTS 3,112,343 A  *  11/1963  Allgeuer ................. C05C 9/005
                                                            252/384
5,653,781 A  *  8/1997   Kayaert .................... B01J 2/16
                                                            71/28
(Continued)

FOREIGN PATENT DOCUMENTS

JP    9-169717 A    6/1997
JP    9-208552 A    8/1997
(Continued)

OTHER PUBLICATIONS

PCT, International Search Report for PCT/JP2016/060884, dated Jun. 21, 2016.

*Primary Examiner* — Amy C Bonaparte
(74) *Attorney, Agent, or Firm* — Orrick, Herrington & Sutcliffe LLP; Joseph A. Calvaruso; K. Patrick Herman

(57) ABSTRACT

The present invention is a urea production method, including: a first concentration step of concentrating an aqueous urea solution; a granulation step of producing solid urea from the concentrated urea solution generated in the first concentration step; a urea recovery step of treating exhaust gas from the granulation step and recovering urea dust in the exhaust gas to generate a recovered aqueous urea solution, the granulation step being configured so as to treat a concentrated urea solution containing an additive; and a second concentration step of concentrating the recovered aqueous urea solution as an additional concentration step, wherein the concentrated recovered urea solution generated in the second concentration step is joined to the concentrated urea solution in the downstream of the first concentration step, and an additive is added downstream of the first concentration step.

15 Claims, 2 Drawing Sheets

(51) Int. Cl.
  *B01J 2/16*  (2006.01)
  *B01J 2/00*  (2006.01)
  *B01J 2/30*  (2006.01)

(56) References Cited

U.S. PATENT DOCUMENTS

| | | | | |
|---|---|---|---|---|
| 5,686,647 A | * | 11/1997 | Chys | C07C 273/04 |
| | | | | 504/327 |
| 5,965,071 A | * | 10/1999 | Fujii | B01J 2/04 |
| | | | | 264/14 |
| 2015/0133689 A1 | * | 5/2015 | Potthoff | C05C 9/005 |
| | | | | 564/63 |
| 2017/0312717 A1 | * | 11/2017 | Scotto | B01J 2/003 |

FOREIGN PATENT DOCUMENTS

| | | |
|---|---|---|
| JP | 2000-001466 A | 1/2000 |
| JP | 3388743 B2 | 1/2003 |
| JP | 2008-538133 A | 10/2008 |
| JP | 2008-280263 A | 11/2008 |
| JP | 2014-530817 A | 11/2014 |
| WO | WO 2013/165245 A1 | 11/2013 |
| WO | WO-2013167245 A1 * 11/2013 ............. C05C 9/005 |
| WO | WO 2014/188371 * 11/2014 |
| WO | WO 2016/047356 A1 | 3/2016 |

\* cited by examiner

Prior Art

UREA PRODUCTION METHOD

TECHNICAL FIELD

The present invention relates to a urea production method. In particular, it relates to a urea production method including a step of producing solid urea by adding an additive to an aqueous solution of synthesized urea. The present invention is a method for reducing adverse effects that may be generated by the addition of an additive in a urea production method.

BACKGROUND ART

Solid urea is one of main products from a urea plant that synthesizes urea. A production step of solid urea is, usually, a process that is set on a downstream side of a urea synthesis step of a urea plant. FIG. 3 is a diagram illustrating a production step of solid urea. In FIG. 3, an aqueous urea solution sent from a urea synthesis step through a line 1 is first supplied to a concentration step A, in which moisture in the aqueous urea solution is removed to give a concentrated urea solution. Then, the concentrated urea solution is supplied to a granulation step B for producing solid urea via a line 2.

In the granulation step B, granular solid urea is produced by use of a known granulation apparatus (line 3). As a known granulation apparatus, a urea granulation apparatus using a fluidized bed or a fluidized/spouted bed or the like is employed. In place of a known granulation apparatus, a prilling urea producing apparatus (such as Prilling Tower) can be used. In the granulation step B, a concentrated urea solution introduced into the granulation apparatus is solidified/cooled by the air supplied from a line 6 to become solid urea (product solid urea). The air supplied in the granulation step B is discharged as exhaust gas (line 7). The exhaust gas in the line 7 contains urea dust generated while the concentrated urea solution was solidified/cooled. A urea concentration in the exhaust gas in the line 7 differs depending on facilities or operating conditions. The urea concentration reaches 70 to 200 $mg/Nm^3$ in a granulation tower system, and 3000 to 10000 $mg/Nm^3$ in a fluidized bed or fluidized/spouted bed system. Therefore, from the viewpoint of prevention of environmental pollution and economical efficiency, there is provided a urea recovery step C of recovering urea dust in the exhaust gas.

With respect to a recovery technology of urea dust in the urea recovery step C, there are, for example as a general method, a packed bed system in which fillings are packed, a venturi system. In these recovery systems, an aqueous urea solution is circulated in a washing tower, and an exhaust gas is made to contact with the aqueous urea solution. As the result of the contact with the aqueous urea solution, the urea dust in the exhaust gas is recovered in the aqueous urea solution.

The exhaust gas from which the urea dust has been recovered in the urea recovery step C is discharged into the air (line 8). The urea concentration in the exhaust gas discharged into the air has been reduced to 20 to 50 $mg/Nm^3$. The aqueous urea solution that has recovered the urea dust in the exhaust gas in the urea recovery step C is sent to the line 1 as a recovered aqueous urea solution (line 10). Meanwhile, make-up water has been added in order to produce the recovered aqueous urea solution (line 9).

Urea in the recovered aqueous urea solution in the line 10 should be treated again in the granulation step B and be solidified/cooled. However, the recovered aqueous urea solution in the line 10 contains much moisture and therefore cannot be treated as it is in the granulation step B. Therefore, it is returned to an upstream side of the concentration step A, concentrated with moisture removed in the concentration step A, and then supplied to the granulation step B. Above is a cycle of respective steps until solid urea is produced from an aqueous solution of synthesized urea.

Incidentally, when solid urea is produced from an aqueous urea solution, it is general to add an additive to a urea solution to be supplied to the granulation step in order to enhance product quality of solid urea. For example, it is known that addition of formaldehyde as an additive leads to generation of a condensation product with urea, and that solid urea having mechanical strength can be produced. As a conventional technology, there are disclosed a method of adding an additive (a condensation product of formalin or formaldehyde with urea) to a urea solution just before the granulation step in a line 5, and concrete conditions in the granulation step when the additive is added (PTL 1). Further, it is sufficient that an additive is contained in the urea solution in the granulation step, and therefore the additive may be added before the concentration step as a line 5'.

CITATION LIST

Patent Literature

PTL 1: Japanese Patent No. 3388743

SUMMARY OF INVENTION

Technical Problem

As described above, the addition of an additive to a urea solution is a useful treatment from the viewpoint of quality control for solid urea. However, in recent years, form of product supply has been diversified along with expansion of use fields of urea. When diversified supply forms or environmental concerns are considered, the use of additives cause following problems.

That is, as is known when FIG. 3 is referred to, when a concentrated urea solution containing an additive is treated in the granulation step B, the additive is contained in the urea contained in a exhaust gas therefrom (line 7). Further, a recovered aqueous urea solution obtained via the recovery step C (line 10) also contains the additive. When the recovered aqueous urea solution is treated in the concentration step A, consequently, a concentrated urea solution therefrom (line 2) always contains an additive component.

The concentrated urea solution generated in the concentration step is frequently used as it is, in addition to being produced as solid urea. For example, the concentrated urea solution is used for an aqueous urea solution for an in-vehicle SCR catalytic converter, which is a purifier of exhaust gas (NOx) from diesel vehicles. As a product name of the aqueous urea solution for an in-vehicle SCR catalytic converter, "AdBlue" (registered trademark) is well known. In addition, the concentrated urea solution is treated as a product that is utilized for a raw material of chemical products, such as melamine. In many of concentrated urea solutions used in these applications, contents of impurities are strictly regulated. Aldehyde or the like, that is an additive for producing solid urea, is regarded as an impurity. Accordingly, using an additive makes it difficult to supply a product for above-described applications.

Further, when the recovered aqueous urea solution containing the additive is sent to the concentration step A, there is a possibility that the additive would be mixed in the water separated in the concentration step (line 4). The water in the line 4 is in a state of steam. Further, the water in the line 4 separated in the concentration step is water containing a minute quantity of urea. The water may be sent to the outside of the urea plant after subjected to a wastewater treatment and reutilized for BFW (boiler water) or the like. However, when the additive is contained in the water in the line 4 separated in the concentration step, it may not be treated by a usual wastewater treatment. Therefore, it becomes necessary to add additional treatment facilities and to consume enormous utilities (such as steam), which leads to economic losses.

Furthermore, the use of additives may affect properties and conditions of solid urea. That is, there is such a risk that moisture derived from the additive raises a moisture concentration of the concentrated urea solution to be supplied to the granulation step and consequently raises moisture in a product. For example, when commercially available formalin (moisture concentration is around 63 mass %) is added to a concentrated urea solution of a moisture concentration of around 4 mass % in order to make solid urea to be a product contain formaldehyde in around 0.5 mass %, the moisture concentration of the concentrated urea solution rises in around 1 mass %, which, as a result, increases the moisture concentration of the solid urea that is a product.

In order to avoid the problem of rise in moisture concentration in solid urea, a method of adding an additive upstream of the concentration step is conceivable. However, with the method, a large quantity of additive is supplied into the concentration step, and therefore the quantity of additive accompanying water separated here becomes large to make the problem of wastewater treatment more remarkable.

The present invention was achieved in the above context, and is a method of improving a urea production method containing a granulation step for producing solid urea from a concentrated urea solution and steps accompanying the granulation step (such as a recovery step). The present inventive method has a step of using an additive. However, the present inventive method can supply a concentrated urea solution not containing the additive as a product. Further, the present inventive method can prevent mixing of the additive in water to be separated in the concentration step. Furthermore, the present inventive method can also suppress undesired increase of the moisture content in solid urea.

Solution to Problem

The present invention that solves the above problems is a urea production method, including: a first concentration step of concentrating an aqueous urea solution; a granulation step of producing solid urea from the concentrated urea solution generated in the first concentration step; a urea recovery step of treating exhaust gas discharged from the granulation step and recovering urea dust in the exhaust gas to generate a recovered aqueous urea solution, the granulation step being configured so as to treat a concentrated urea solution containing an additive; and a second concentration step of concentrating the recovered aqueous urea solution by removing at least a part of water in the recovered aqueous urea solution to generate a concentrated recovered urea solution, wherein the concentrated recovered urea solution generated in the second concentration step is joined to the concentrated urea solution in the downstream of the first concentration step, and an additive is added in the downstream of the first concentration step.

The present invention was made based on the findings obtained by meticulous studies by the present inventors, and has following characteristics. Meanwhile, in the present application, a "urea solution" includes both molten urea and an aqueous urea solution. The molten urea may contain moisture. Further, in the present application, "downstream" means a flow (line) at or after an outlet of an arbitrary step, and is a flow of any of at least one of gas or liquid or solid, or a mixture thereof that is communicated with the outlet. The meaning of "upstream" is similarly a flow at or prior to the inlet of the step, and is a flow of any of at least one of gas or liquid or solid, or a mixture thereof that is communicated with the inlet.

The present invention is characterized by having two concentration steps of the first concentration step and the second concentration step. The first concentration step is, similarly to a conventional method, a step of concentrating an aqueous urea solution to generate a concentrated urea solution. The second concentration step is an additional concentration step of removing moisture in the recovered urea solution from the urea recovery step and concentrating the solution to generate a concentrated recovered urea solution. Setting the second concentration step enables the recovered aqueous urea solution to be concentrated to a suitable moisture content and to supply the same to the granulation step.

Then, in the present invention, the concentrated recovered urea solution concentrated in the second concentration step is joined to a downstream side of the first concentration step and supplied to the granulation step. Further, addition timing of an additive is also set to a downstream side of the first concentration step. This can avoid mixing of the additive in the system of the first concentration step. As the result, a concentrated urea solution not containing the additive can be obtained. Then, the concentrated urea solution can be suitably used as a raw material of various products derived from urea, such as AdBlue and melamine.

Further, in the second concentration step in the present invention, water is removed from the recovered aqueous urea solution. The water contains the additive. The water can be used as make-up water for generating the aqueous urea solution in the urea recovery step, and, therefore, the whole or a part thereof can be sent to the urea recovery step. Thus setting the second concentration step can avoid mixing of the additive in the water obtained in the first concentration step. Accordingly, it becomes unnecessary to apply an extraordinary treatment to the water obtained in the first concentration step. The water is reutilized for BFW etc. after a usual wastewater treatment.

In the present invention, a point at which an additive is added can be set arbitrarily as long as the point lies downstream of the first concentration step and thereafter. That is, the whole or a part of an additive may be added between the first concentration step and the granulation step. Further, the whole or a part of an additive may be added between the urea recovery step and the second concentration step. The setting of an addition point of additive can reduce the effect by moisture derived from the additive. The point will be described in detail later.

Advantageous Effects of Invention

As described above, the present invention sets the second concentration step, and optimizes the addition point of additive, which can eliminate adverse effects of an additive, while using the additive when producing solid urea.

DESCRIPTION OF EMBODIMENTS

Figure 1:
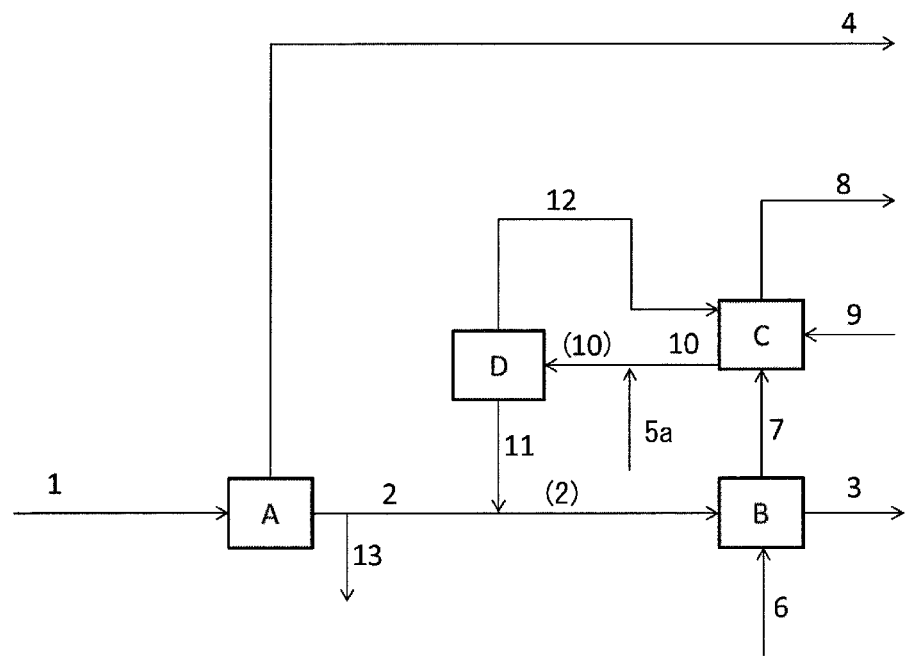
FIG. 1 is a diagram that schematically illustrates a configuration of processes according to an embodiment of producing solid urea from an aqueous urea solution.

The present invention will be described more concretely with embodiments thereof. FIG. 1 is a diagram illustrating a urea production method that is an embodiment of the present invention. In the urea production method, solid urea is produced as a main product by treating an aqueous solution of urea synthesized in an upstream urea synthesis section, and a concentrated urea solution is also produced as a product. A urea synthesis method in the urea synthesis section is not particularly limited, and properties and conditions of the aqueous urea solution produced there, such as urea concentration, are also not limited.

The aqueous urea solution is sent to the first concentration step A via the line 1. In the concentration step A, water (steam) is removed from the aqueous urea solution with a concentration apparatus, such as an evaporator, to concentrate the aqueous urea solution until the urea concentration becomes around 94 to 99.7 mass %. The concentrated urea solution generated in the concentration step A is supplied to the granulation step B via the line 2.

The granulation step B produces a product solid urea in the line 3 from the concentrated urea solution by use of a granulation apparatus, such as a urea granulation apparatus using a rotary drum, fluidized bed or fluidized/spouted bed. In place of the granulation apparatus, a urea prill producing apparatus may be used. In these granulation apparatuses, an operation of solidifying/cooling the urea solution is performed. To this end, the air is introduced into the granulation step B from the line 6. The introduced air is discharged from the granulation step B as a exhaust gas while accompanying urea dust and is introduced into the urea recovery step C via the line 7.

In the urea recovery step C, the exhaust gas has been introduced into a recovery apparatus, such as a washing tower (scrubber), via the line 7. In the washing tower, for example, an aqueous urea solution in around 10 to 50 mass % is circulated. The aqueous urea solution is made to contact with the exhaust gas, and thereby the urea dust in the exhaust gas is dissolved/absorbed in the aqueous urea solution. The exhaust gas washed in the urea recovery step C is discharged into the air from the line 8. At this time, the exhaust gas to be discharged into the air takes in water in the urea recovery step, and therefore make-up water is replenished from the line 9. Then, the aqueous urea solution that has absorbed/ recovered urea is introduced into a second concentration step D via the line 10 as a recovered aqueous urea solution.

The recovered aqueous urea solution via the line 10 has a large moisture content, and therefore it cannot be supplied to the granulation step as it is. Consequently, the second concentration step D removes at least a part of the moisture from the recovered aqueous urea solution to generate a concentrated recovered urea solution. Also in the second concentration step D, a concentration apparatus, such as an evaporator, is used. The moisture content in the concentrated recovered urea solution generated in the second concentration step D may be the same as or different from that in the concentrated urea solution generated in the first concentration step. The concentrated recovered urea solution is joined to the concentrated urea solution from the line 2 via a line 11. On the other hand, at least a part of the water having been removed from the recovered aqueous urea solution in the second concentration step D, while containing a part of urea and an additive, is supplied as make-up water in the urea recovery step C via a line 12. At this time, the whole quantity of water removed from the recovered aqueous urea solution in the second concentration step D may be supplied to the urea recovery step C.

Meanwhile, in the second concentration step D, there may occur hydrolysis or a biuret generation reaction in a part of the urea to generate ammonia. On this occasion, consequently, the ammonia is sent to the urea recovery step C via the line 12. The ammonia is not absorbed into the aqueous urea solution. The ammonia is contained in the exhaust gas in the line 8. Consequently, an ammonia concentration in the exhaust gas in the line 8 may rise. As a measure for preventing this, there is a method of providing the urea recovery step C with a function of recovering the ammonia in a form of a salt. For example, there is a method that adds acid to an aqueous urea solution circulating inside the urea recovery step C to adjust pH to around pH 2 to 6, and recovers the ammonia in a form of a salt. At this time, the recovered salt is mixed in the recovered aqueous urea solution, but its quantity can be estimated to be extremely small, and therefore the salt can be treated in the second concentration step D and mixed into products. Further, as another measure of recovering the ammonia in the urea recovery step C, there is also a method that supplies the exhaust gas from the urea recovery step C to a washing tower in which an acid solution of around pH 2 to 6 is circulated, and thereby recovers the ammonia in a form of a salt. When the method is employed, the salt recovered in the washing tower in which an acid solution is circulated may be mixed into products, or may not be mixed but treated as a by-product.

In the present invention, an additive is added downstream of the first concentration step. In the embodiment in FIG. 1, an additive is added from a line 5a that lies upstream of the second concentration step. The additive is mixed with the recovered aqueous urea solution of the line 10, introduced into the second concentration step D and concentrated, and supplied to the granulation step via the line 11.

As described above, in the embodiment, an additive is added upstream of the second concentration step. An advantage of adding the additive at this point lies in that moisture of the additive is preliminarily removed and the additive can be supplied to the granulation step B. As described above, in a conventional method, for example, there is a risk that, when an aqueous solution such as formalin is added as an additive, the moisture is introduced as it is into the granulation step. In the embodiment of the present invention, the moisture in the additive can be removed in the second concentration step, and therefore excessive moisture is not introduced into the granulation step B. Hereby, the moisture content in solid urea of product can be made proper.

Further, an advantage of adding an additive in the line 5a also lies in that retention time of the additive can be secured. It is necessary for an additive to secure sufficient retention time in a state mixed with urea depending on the type of the additive. For example, it is described in PTL 1 that, when a water-soluble addition product or condensation product of formaldehyde with urea is to be added, a dust generation quantity can be reduced by setting the retention time to 25 sec to 20 min. In conventional techniques, shortage of the retention time may cause a problem. In contrast, the additive is concentrated while being contacted with urea with sufficient retention time and supplied to the granulation step, by introducing the additive in the second concentration step D with the recovered aqueous urea solution as in the embodiment shown in FIG. 1.

Then, the present invention can obtain, as a product, a concentrated urea solution containing no additive, by drawing the concentrated urea solution from a flow that lies downstream of the first concentration step and that lies upstream of both a joining point with the concentrated recovered urea solution generated in the second concentration step and a point at which an additive is added. Concretely, the concentrated urea solution not containing the additive can be obtained as a product from a line 13 lying at the outlet of the first concentration step A in FIG. 1. The additive added from the line 5a is added to the concentrated urea solution with the concentrated recovered urea solution via the line 11, and thus the additive is not contained in an upstream side of the joining point of the line 2 with the line 11. Consequently, it is possible to take out, as a product, the concentrated urea solution not containing the additive out of the line 13.

Further, in the present invention, no additive is mixed in the system of the first concentration step A. Accordingly, no additive is mixed in the water in the line 4, which has been removed from the aqueous urea solution in the first concentration step A. The water in the line 4 can be reutilized for BFW etc. after an ordinary wastewater treatment, without a special treatment.

Figure 2:
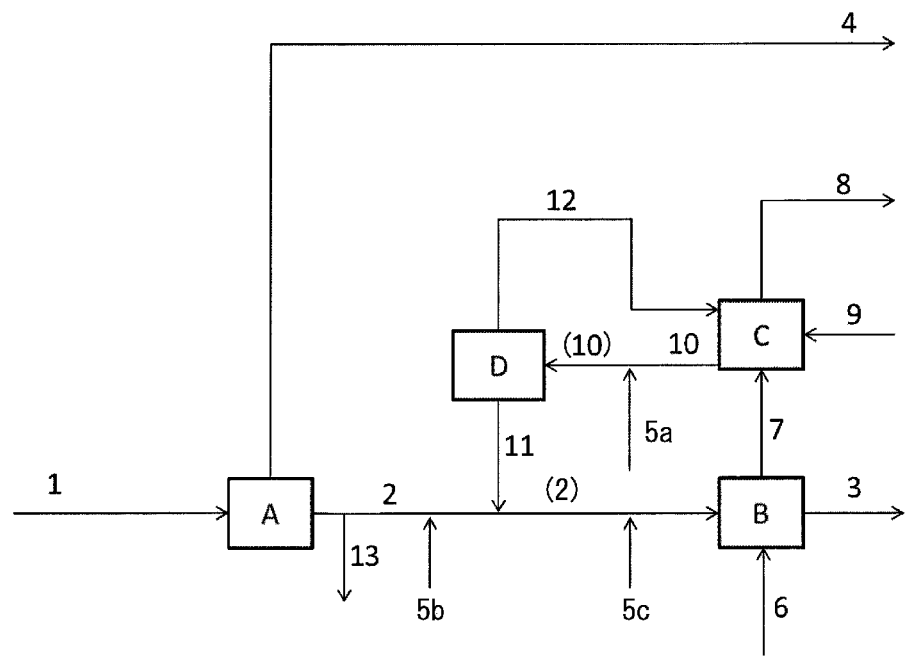
FIG. 2 is a diagram that schematically illustrates a configuration of processes according to another embodiment having a plurality of lines for adding an additive.

The point at which an additive is added in the present invention is not particularly limited as long as it lies downstream of the first concentration step. Further, the addition point is not limited to one, but a plurality of points can be set. FIG. 2 is a diagram showing a plurality of suitable lines for adding an additive. Adding an additive via at least any one point of the lines 5a, 5b, and 5c in FIG. 2 can obtain a urea solution containing no additive from the line 13.

Further, it is possible to solve the problem of moisture derived from an additive and the problem of securing the retention time, by utilizing at least the line 5a. At this time, an additive may be added only from the line 5a (the same as in FIG. 1), but it is also possible to add the additive also from other lines (lines 5b, 5c) while partially adding the necessary quantity of additive in the line 5a.

Example

Figure 3:
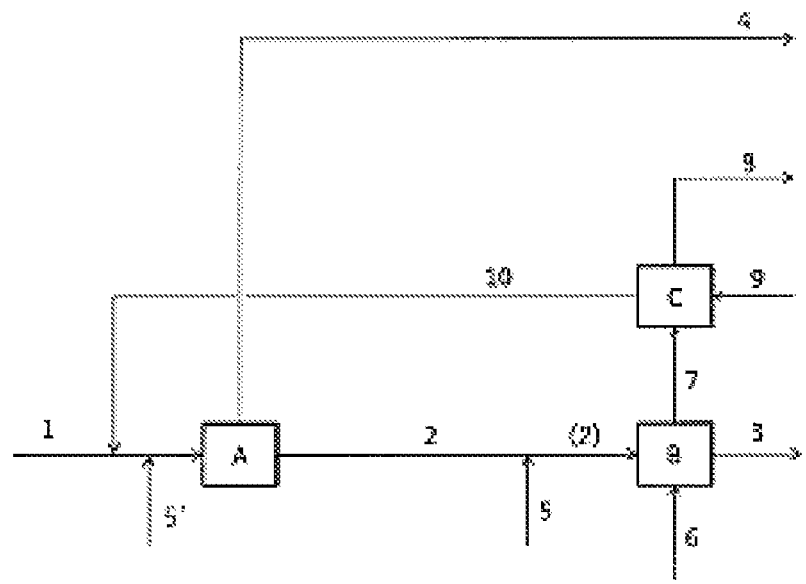
FIG. 3 is a diagram that schematically illustrates a configuration of a conventional process of producing solid urea from an aqueous urea solution.

Next, concrete studies were made about the embodiment in FIG. 1, with reference to material balance in respective lines. Here, assuming a urea plant provided with a urea granulation apparatus of a fluidized/spouted bed system having producing ability of 3500 ton/day of solid urea, there were calculated approximate values of the material balance of respective lines in instances according to flows in FIG. 1 (Example), and FIG. 3 (Comparative Example). In the calculation in Example in FIG. 1, the taking out of the concentrated urea solution in the line 13 was not performed. In Comparative Example in FIG. 3, an additive was added from the line 5. First, material balances in respective lines in Example (FIG. 1) are shown in Table 1, and material balances in respective lines in Comparative Example (FIG. 3) are shown in Table 2.

TABLE 1

| Line No. | Urea | Water | Ammonia | Formaldehyde | Flow rate | Air Flow rate | % |
|---|---|---|---|---|---|---|---|
| 1 | 69.5% | 30% | 0.5% | 0% | 210 t/h | — | — |
| 2 | 96% | 4.0% | 0% | 0% | 151 t/h | — | — |
| (2) | 95.6% | 4.0% | 0% | 0.4% | 158 t/h | — | — |
| 3 | 99.2% | 0.3% | 0% | 0.5% | 146 t/h | — | — |
| 4 | 1% | 97% | 2% | 0 ppm | 59 t/h | — | — |
| 5a | 0% | 63% | 0% | 37% | 2 t/h | — | — |
| 6 | 0% | 100% | 0% | 0% | 45 t/h | 955000 Nm$^3$/h | — |
| 7 | 10% | 90% | 0% | 0.04% | 57 t/h | 955000 Nm$^3$/h | — |
| 8 | 0% | 100% | 0% | 0% | 77 t/h | 955000 Nm$^3$/h | — |
| 9 | 0% | 100% | 0% | 0% | 25 t/h | — | — |
| 10 | 44.8% | 55% | 0% | 0.2% | 13 t/h | — | — |
| (10) | 39% | 56% | 0% | 5% | 15 t/h | — | — |
| 11 | 86% | 4.0% | 0% | 10% | 7 t/h | — | — |
| 12 | 0% | 99.9% | 0.1% | 0% | 8 t/h | — | — |

(2) Line 2 after joining with line 11
(10) Line 10 after addition of an additive (line 5a)

TABLE 2

| Line No. | Urea | Water | Ammonia | Formaldehyde | Flow rate | Air Flow rate | % |
|---|---|---|---|---|---|---|---|
| 1 | 69.5% | 30% | 0.5% | 0% | 210 t/h | — | — |
| 2 | 96% | 4.0% | 0% | 0.02% | 157 t/h | — | — |
| (2) | 94.9% | 4.7% | 0% | 0.4% | 159 t/h | — | — |
| 3 | 99.0% | 0.5% | 0% | 0.5% | 146 t/h | — | — |
| 4 | 1% | 97% | 2% | 3 ppm | 66 t/h | — | — |
| 5 | 0% | 63% | 0% | 37% | 2 t/h | — | — |
| 6 | 0% | 100% | 0% | 0% | 45 t/h | 955000 Nm$^3$/h | — |
| 7 | 10% | 90% | 0% | 0.04% | 58 t/h | 955000 Nm$^3$/h | — |
| 8 | 0% | 100% | 0% | 0% | 77 t/h | 955000 Nm$^3$/h | — |
| 9 | 0% | 100% | 0% | 0% | 32 t/h | — | — |
| 10 | 44.8% | 55% | 0% | 0.2% | 13 t/h | — | — |

(2) Line 2 after joining with line 5

Formalin that is an additive is added via the line 5a. As is known from Table 1, the moisture in formalin is mostly removed in the second concentration step D along with the recovered aqueous urea solution in the line 10. Therefore, a water content in the line (2) supplied to the granulation step B has been adjusted in an appropriate range. Then, the concentrated recovered urea solution supplied by the line 11 from the second concentration step D contains an appropriate quantity of additive, and is supplied to the granulation step B after the reaction with urea has progressed.

Further, the additive supplied from the line 5a circulates through a loop of the second concentration step D→ the granulation step B→ the recovery step→ the second concentration step D. Therefore, no additive is contained in the system of first concentration step A. Consequently, It is possible to obtain the concentrated urea solution not containing the additive in the line 2 (from Table 1, it is a urea solution of 0 mass % of formaldehyde and 96 mass % of urea concentration). The concentrated urea solution can be drawn from the line 13 as a product of a urea solution (the composition is the same as that in the line 2). Further, no additive is also contained in the water in the line 4 taken out in the first concentration step A.

In contrast, in Comparative Example in Table 2, the moisture content in the concentrated urea solution rises from 4 mass % (line 2) to 4.7 mass % (line (2)) by the effect of formalin added via the line 5. Consequently, the moisture content in a product solid urea (line 3) may be affected.

Further, in Comparative Example, the additive reaches the concentration step A from the line 10, from the exhaust gas in the granulation step B (line 7) via the recovery step C. Therefore, 0.02 mass % of formaldehyde is contained in the concentrated urea solution from the concentration step A (line 2).

It will be examined whether the concentrated urea solution collected in Comparative Example can be used as various urea products. As an example, applicability as a raw material of AdBlue will be examined. In Deutsche Industrie Normenausschuss: DIN 70070 known as the standard of AdBlue, there is determined such regulation as urea concentration: 31.8 mass % (min.) to 33.2 mass % (max.) and aldehyde as an impurity: 5 mg/kg max. for the aqueous urea solution. Accordingly, in the concentrated urea solution in the line 2 in Comparative Example (formaldehyde quantity: 0.02 mass %), the aldehyde quantity does not satisfy the standard even when it is diluted with water. Accordingly, it is known that the urea solution is not suitable for a raw material of AdBlue.

Furthermore, in Comparative Example, formaldehyde is also contained in an extremely small amount in the water taken out in the concentration step A (line 4). It is difficult to cleanse the water by an ordinary wastewater treatment alone and, in order to reutilize the water, further treatment is necessary.

INDUSTRIAL APPLICABILITY

The present invention can produce solid urea while avoiding adverse effects caused by the use of an additive, such as mixing of the additive in the concentration step or mixing of moisture derived from the additive in the granulation step. The present inventive urea production method can produce, also as a product, a concentrated urea solution having reduced impurities, together with high-quality solid urea of a product.

The invention claimed is:
1. A urea production method, comprising:
a first concentration step of concentrating an aqueous urea solution sent from a urea synthesis step to generate a concentrated urea solution;
a granulation step of producing solid urea from the concentrated urea solution generated in the first concentration step and discharging an exhaust gas containing urea dust;
a urea recovery step of washing the exhaust gas discharged from the granulation step with a circulating aqueous urea solution to recover urea dust in the exhaust gas, generate a recovered aqueous urea solution in which the majority of the urea dust is dissolved or absorbed, and discharge a washed exhaust gas,
an additive addition step whereby a separate additive, not generated in whole or in part by the urea recovery step, is added to the recovered aqueous urea solution, and
a second concentration step of concentrating the recovered aqueous urea solution containing the separate additive by removing at least a part of the water in the recovered aqueous urea solution to generate a concentrated recovered urea solution, wherein
the granulation step is configured to treat a concentrated urea solution containing the additive;
the separate additive is formalin or a condensation product of formaldehyde with urea and does not contain recovered urea dust, and
the concentrated recovered urea solution generated in the second concentration step is joined to the concentrated urea solution downstream of the of the first concentration step.

2. The urea production method according to claim 1, wherein at least a part of the water removed from the recovered aqueous urea solution in the second concentration step is sent to the urea recovery step.

3. The urea production method according to claim 1, wherein all the water removed from the recovered aqueous urea solution in the second concentration step is sent to the urea recovery step.

4. The urea production method according to claim 1, wherein the separate additive is additionally added to the concentrated urea solution downstream of the first concentration step and upstream of the granulation step.

5. The urea production method according to claim 1, further comprising drawing a part of the concentrated urea solution from downstream of the first concentration step before the concentrated recovered urea solution generated in the second concentration step is joined, and the rest of the concentrated urea solution is sent to the granulation step.

6. The urea production method according to claim 2, wherein the separate additive is additionally added to the concentrated urea solution downstream of the first concentration step and upstream of the granulation step.

7. The urea production method according to claim 3, wherein the separate additive is additionally added to the concentrated urea solution downstream of the first concentration step and upstream of the granulation step.

8. The urea production method according to claim 2, further comprising drawing a part of the concentrated urea solution from downstream of the first concentration step before the concentrated recovered urea solution generated in the second concentration step is joined, and the rest of the concentrated urea solution is sent to the granulation step.

9. The urea production method according to claim 3, further comprising drawing a part of the concentrated urea solution from downstream of the first concentration step before the concentrated recovered urea solution generated in the second concentration step is joined, and the rest of the concentrated urea solution is sent to the granulation step.

10. The urea production method according to claim 4, further comprising drawing a part of the concentrated urea solution from downstream of the first concentration step before both the concentrated recovered urea solution generated in the second concentration step is joined and the additional additive is added, and the rest of the concentrated urea solution is sent to the granulation step.

11. The urea production method according to claim 6, wherein
    a part of the concentrated urea solution is drawn downstream of the first concentration step before both the concentrated recovered urea solution generated in the second concentration step is joined to the concentrated urea solution and the additional separate additive is added, and
    the remainder of the concentrated urea solution is sent to the granulation step.

12. The urea production method according to claim 7, wherein
    a part of the concentrated urea solution is drawn downstream of the first concentration step before both the concentrated recovered urea solution generated in the second concentration step is joined to the concentrated urea solution and the additional separate additive is added, and
    the remainder of the concentrated urea solution is sent to the granulation step.

13. The urea production method according to claim 1, wherein an acid is added to the circulating aqueous urea solution during the urea recovery step to adjust the pH of the circulating aqueous urea solution to 2 to 6 such that the circulating aqueous urea solution recovers ammonia in a form of a salt.

14. The urea production method according to claim 1, wherein water is obtained in the first concentration step by concentrating the aqueous urea solution and is reutilized as boiler water.

15. The urea production method according to claim 13, wherein water is obtained in the first concentration step by concentrating the aqueous urea solution and is reutilized as boiler water.

\* \* \* \* \*